US005759946A

United States Patent [19]

Hoang et al.

[11] Patent Number: 5,759,946
[45] Date of Patent: Jun. 2, 1998

[54] CATALYSTS FOR OXIDATIVE DEHYDROGENATION OF HYDROCARBONS

[75] Inventors: Mahn Hoang, South Clayton; Kerry C. Pratt, North Ringwood; Joseph Mathews, Armadale, all of Australia

[73] Assignees: Commonwealth Scientific and Industrial Research Organisation, Australian Capital Territory; Monash University, Victoria, both of Australia

[21] Appl. No.: 620,355

[22] Filed: Mar. 22, 1996

[30] Foreign Application Priority Data

Mar. 22, 1995 [AU] Australia ................................. PN1901

[51] Int. Cl.[6] ............................... B01J 23/10; B01J 23/26
[52] U.S. Cl. ........................ 502/303; 502/302; 502/304; 502/319
[58] Field of Search ...................... 502/174, 302, 502/303, 304, 305, 306, 317, 319, 340, 349

[56] References Cited

U.S. PATENT DOCUMENTS 3,450,789  6/1969  Kehl et al. .......................... 260/680
5,376,613  12/1994 Dellinger et al. .................... 502/304

Primary Examiner—Glenn Caldarola
Assistant Examiner—Thuan D. Dang
Attorney, Agent, or Firm—Sughrue, Mion, Zinn, Macpeak & Seas, PLLC

[57] ABSTRACT

A catalyst for the oxidative dehydrogenation of hydrocarbons which includes a chromium oxide supported on a lanthanide carbonate, and a process for producing the catalyst; the catalyst is useful in a process for the oxidative dehydrogenation of hydrocarbons.

17 Claims, No Drawings 5,759,946

1

CATALYSTS FOR OXIDATIVE DEHYDROGENATION OF HYDROCARBONS

FIELD OF THE INVENTION

This invention relates to catalysts and processes for the production of olefins and partial oxidation products of hydrocarbons by the catalytic oxidative dehydrogenation of such hydrocarbons.

BACKGROUND OF THE INVENTION

The production of olefinic hydrocarbons and partial oxidation products is a very important industrial process. Olefins and hydrocarbon derivatives containing oxygen are very important intermediates in the petrochemical industry, and substantial increases in demand in future are expected. Substantial efforts be therefore been directed towards the production of such compounds by catalytic dehydrogenation and oxidation. Reactions of commercially interest include:

Methanol, formaldehyde and higher hydrocarbons from methane.

Ethane to ethylene, ethylene oxide.

Propane to propylene, propylene oxide and acrylic acid

Iso-butane to iso-butylene.

n-butane to butenes and maleic anhydride.

Iso-butene, propylene to methacrylonitrile, acylonitrile.

Ethyl benzene to styrene.

DESCRIPTION OF RELATED ART

It is known from the prior art that hydrocarbons can be converted to unsaturated materials by various dehydrogenation processes, including the following:

1. Dehydrogenation:

(I) The Oleflex process, based on the synergistic combination of dehydrogenation of $C_1$ to $C_{14}$ and catalytic reforming of naphtha. (ii) The Catofin process, developed in 1940s, in which the hydrocarbon is vaporised with steam, preheated to the reaction temperature and then fed to the reactor. (iii) The Phillips Steam Activated Reforming dehydrogenation, known as the Star process, developed in late 1970s and early 1980s. Steam is used as diluent, feed is preheated before feeding to the reactor. (iv) The FBD-4 process, using the Snamprogetti-Yarsintez process.

Among the best known catalysts for dehydrogenation are chromium- and platinum-based catalysts; both may be optionally supported on such materials as alumina, zirconia and the like. The platinum-based catalysts exhibit a tendency to skeletal isomerisation, producing a small quantity of isomerisation products.

The dehydrogenation reaction is strongly endothermic and the conversion per pass is limited by thermodynamic equilibrium. This is a high energy consumption process and many undesirable reactions occur such as feedstock crack and coking of the catalyst.

2. Oxidative Dehydrogenation:

This process has been extensively investigated because in theory it permits more dehydrogenation to occur. Since water is a by product instead of hydrogen, this process does not have a thermodynamic equilibrium limitation and coke formation can be eliminated. However, it is a major challenge to achieve high conversion to product, i.e. to achieve maximum yields of desired product(s) while minimising the combustion activity which may occur at the high temperatures required to activate hydrocarbons. Therefore, the production of olefins or partial oxidation products from the corresponding alkanes by oxidative dehydrogenation has not so far been successful. The conversion of n-butane to maleic anhydride is the only successful industrial practice in selective oxidation of alkanes.

It is further known that the oxidative dehydrogenation can be carried out more efficiently in the presence of halogens or halogen-based compounds, for example iodine, hydrogen iodide or ammonium iodide. However, this process has not gained commercial success due to the prohibitive cost of iodine.

Industrial interest has stimulated numerous investigations into methods of improving the performance of catalysts, particularly in relation to the influence of catalyst texture.

Accordingly, it is an object of the present invention to overcome, or at least alleviate, the difficulties presented by prior art processes as outlined above.

SUMMARY OF THE INVENTION

The present invention provides a novel catalytic system which catalyses the oxidative dehydrogenation of hydrocarbons, e.g. alkanes to corresponding alkenes or partial oxidation products.

The catalyst system of the present invention, is characterised by the fact that it catalyses oxidative dehydrogenation selectively at relatively low temperatures at which secondary reactions are minimised. Such highly selective catalysts may also find further applications in the catalytic separation of hydrocarbons or in synergistic combinations with other reactions.

DESCRIPTION OF THE PREFERRED EMBODIMENTS

According to a first aspect of the present invention, there is provided a novel catalyst for the oxidative dehydrogenation of hydrocarbons which comprises a chromium oxide supported on a lanthanide carbonate.

The supported chromium oxide can be present in any oxidation state and can be chemically bound to the support surface or present as a separate crystalline phase.

The atomic ratio of chromium to lanthanide may be in the range of approximately 0.1:99.9 to 99.9–0.1, but preferably lies in the range of 1:99 to 20:80.

The catalyst may also contain one or more additional components which alter its activity and selectivity. These additional components may be selected from oxides or carbonates of the metals of Groups IA and IIA, the transition metals, the lanthanides or mixtures thereof.

The catalysts of the invention may be prepared by any suitable known technique, such as co-precipitation, impregnation or physical mixing.

In this context:

"co-precipitation" means the co-precipitation of the chromium oxide and lanthanide carbonate, or the precursors, e.g. from aqueous solutions of the metal salts;

"impregnation" means impregnation of a solid form of one of the catalyst components (or a precursor thereof) with, e.g., an aqueous solution of a salt of the other metal;

"physical mixing" includes mixing the catalyst components or precursors thereof;

"precursor" means any compound of the metal(s) which is capable of being converted to the required oxide or carbonate by physical and/or chemical treatment.

The preferred process is co-precipitation and accordingly, in a further aspect, the invention provides a process for producing a catalyst, which comprises the steps of:

providing a solution containing ions of chromium and one or more lanthanides;

adding a source of carbonate ions to the solution to thereby co-precipitate carbonates of the two metals;

separating the precipitate from the solution;

washing and drying the precipitate;

and heating the precipitate to a temperature sufficient to activate the catalyst.

The solution containing the chromium and lanthanide ions may be prepared from any suitable source(s), such as solid, hydrated or anhydrous compounds containing any suitable anions including chloride, sulphate, nitrate, or carboxylic acid anions such as acetate, or the like. Alternatively, a solution of the desired metal(s) may be produced by dissolving an insoluble source such as the metal, oxide, carbonate or mixtures thereof, in a stoichiometric or in an excess amount of an acid, containing any of the above anions.

The additional components defined above may be incorporated into the catalyst in the required proportions by adding as pure solids (mixing) or liquids (impregnation) or by co-precipitation with the primary catalyst components, as described above.

In a preferred embodiment, the overall process for preparation of the catalyst is comprised of the following steps:

(i) Mixing a solution containing the mixed metal ions with a solution containing carbonate or bicarbonate ions, to precipitate the metal carbonates. The source of carbonate or bicarbonate can be an aqueous solution of any alkali metal or ammonium carbonate salt. A particularly convenient source of carbonate ions, with regard to ease of subsequent purification, is commercial "ammonium carbonate", which comprises a mixture of ammonium bicarbonate and ammonium carbamate in the ratio of about 5:1. The precipitation may be carried out at any temperature from ambient to 60° C. and in any suitable manner.

(ii) Separating the precipitate (as a gel) from reaction mixture by any standard method, such as centrifugation or filtration. Washing the gel repeatedly with distilled water, followed by subsequent dehydration by washing the gel with a water miscible organic solvent such as an alcohol or ketone, preferably acetone.

(iii) Removing the organic solvent from the solid material, e.g. by drying under a stream of air to dryness.

(iv) Converting the catalyst precursor into the activated catalyst by an appropriate thermal treatment. This activation step can be carried out by heating in air or any inert atmosphere up to 600° C., but preferably between 200°–450° C.

The catalyst surface area is proportional to chromium loading and varies from 20 to 300 m$^2$/g.

According to a further aspect of the invention, there is provided a process for the oxidative dehydrogenation of hydrocarbons, which involve the use of a catalyst as defined above.

The reaction which may be carried out over the catalyst system provided by this invention include the following:

Methane activation.

Oxidative dehydrogenation of alkanes, especially light alkanes, to the corresponding alkenes and oxygenates.

Ethyl benzene to styrene.

For oxidative dehydrogenation of light alkanes, as the gaseous hydrocarbon, there may suitably be used methane, ethane, propane, butanes or mixtures thereof. For the higher (liquid) hydrocarbons, the operation may be carried out in conjunction with vaporisation of the hydrocarbon.

The process of the invention can be carried out in the presence or absence of molecular oxygen-containing gas and in any suitable reactor, such as a fixed-bed, fluidised-bed or a riser reactor.

When the process is carried out in the absence of molecular oxygen, the catalyst is regenerated, as required, by contact with air or other oxygen-containing gases. The regeneration process can be carried out at the normal reaction temperature or higher.

To further illustrate the process of this invention, the following examples are provided. It should be understood that the details thereof are not to be regarded as limitations and various modifications may be made without departing from the spirit of the invention.

I. Preparation of Supported Chromia/Lanthanum Carbonate Catalyst:

This example illustrates the preparation of catalyst containing supported chromia/lanthanum carbonate with Cr/La atomic ratio of 10/90, or 3.5 wt % $Cr_2O_3/La_2(CO_3)_3$, (i.e. 3.5 wt % $Cr_2O_3$ and 96.5 wt % $La_2(CO_3)_3$).

A mixture of $Cr(NO_3)_3.9H_2O$ (0.8 g) and $La(NO_3)_3.6H_2O$ (7.9 g) in $H_2O$ (250 ml) was slowly added to an aqueous solution of commercial ammonium carbonate (5 g in 250 ml $H_2O$) with vigorous stirring. After addition, the precipitate was separated by centrifugation and washed twice with 0.5 l of water and then twice with 0.5 l acetone. Initial drying in an air stream at room temperature was followed by calcination in air at 250° C. for 4 hr.

II. Catalytic Oxidative Dehydrogenation of Hydrocarbons:

The following examples illustrate a preferred embodiment of the present invention, that is the production of iso-butene from iso-butane in a pulse mode reactor. The following conditions were employed:

Temperture: 200°–280° C.

Catalyst: 0.200 mg

Pressure: 150 KPa

Pulse size: 4.25 μmol iso-butane

Space velocity: 0.102 mol g$^{-1}$ h$^{-1}$

EXAMPLE 1

The catalyst was prepared in accordance with the procedure described above. In this example, the catalyst, consisting of 10 wt % $Cr_2O_3/La_2(CO_3)_3$ calcined in air at 300° C. for 4 hr, was packed in the pulse reactor and heated to 230° C. After 6 pulses of iso-butane were introduced, an average selectivity for iso-butene of 95% was obtained, yielding 0.54 g iso-butene/kg catalyst. The average carbon balance was 97%. The catalyst activity decreased by >50% over the first 6 pulses; the catalyst was regenerated by exposure to 2 pulses of pure oxygen at the reaction temperature (230° C.). The results are summarised in Table 1.

EXAMPLE 2

The same catalyst was tested at temperatures of 220°, 230°, 240°, 250° and 260° C. The iso-butene yields were 0.52, 0.54, 0.71, 0.71, 0.69, 0.60 g/kg catalyst respectively. This example shows the effect of reaction temperature on the yield of iso-butene.

EXAMPLE 3

Five catalysts consisting of 1.4, 3.5, 5.5, 10, 25 wt % $Cr_2O_3$ respectively supported on $La_2(CO_3)_3$ were tested at 240° C. After 6 pulses, the iso-butene yields were 0.65, 0.76, 0.76, 0.70, 0.15 g/kg catalyst respectively. $La_2(CO_3)_3$ alone was inactive for the reaction at 240° C. This example shows the effect of chromium loading on the performance of the catalyst and the results are summarised in Table 2.

EXAMPLE 4

Catalysts consisting of 3.5 wt % $Cr_2O_3$ calcined at 250°, 300°, 350° and 400° C. in air were tested at 240° C. After 6 pulses the iso-butene yields were 0.87, 0.76, 0.61, 0.14 g/kg catalyst respectively. This example shows the effect of calcination temperature.

EXAMPLE 5

A catalyst consisting of 3.5 wt % $Cr_2O_3/La_2(CO_3)_3$ was calcined in He at 300° C. for 4 hr and tested at 240° C. After 6 pulses, the average selectivity was 99% and the yield of iso-butene was 0.68 g/kg catalyst.

EXAMPLE 6

A catalyst consisting of 3.5 wt % $Cr_2O_3/La_2(CO_3)_3$ was impregnated with $(NH_4)_2Ce(NO_3)_6$, calcined at 300° C. to yield a 0.1 wt % $CeO_2$ promoted catalyst and tested at 240° C. After 6 pulses, an average selectivity was 99% and the iso-butene yield was 0.84 g/kg catalyst.

EXAMPLE 7

A catalyst was prepared as in Example 6, but the promoter was 0.1 wt % $Na_2O$, prepared by impregnation with $NaNO_3$, prior to calcination. The average selectivity was 99% and the iso-butene yield was 0.52 g/kg catalyst.

TABLE 1

Pulse Reactor test for 25 Wt % $Cr_2O_3/La_2(CO_3)_3$
Pulse size: 4.25 μmol isobutane, 240° C.

| | Activity (μmol/$_{iso-butene}$/g catalyst) | | |
|---|---|---|---|
| Pulse No. | Initial activity | 1$^{st}$ regeneration | 2$^{nd}$ regeneration |
| 1 | 3.01 | 3.1 | 3.1 |
| 2 | 2.59 | 2.2 | 2.25 |
| 3 | 2.03 | 1.70 | 1.65 |
| 4 | 1.67 | 1.36 | 1.57 |
| 5 | 1.65 | 1.36 | 1.39 |
| 6 | 1.50 | 1.31 | 1.31 |

TABLE 2

Cumulative yield of iso-butene as a function of chromia loading

| Chromia Loading (Wt %) | Yield of iso-butene (g/Kg catalyst) |
|---|---|
| 0 | 0 |
| 5 | 0.65 |
| 10 | 0.76 |
| 15 | 0.76 |
| 25 | 0.70 |
| 50 | 0.15 |

EXAMPLE 8

A catalyst was prepared in accordance with the procedure described above using $Pr(NO_3)_3$ as a starting material. In this example, the catalyst, consisting of 10% mol $Cr_2O_3$ supported on $Pr_2(CO_3)_3$, calcined in air at 300° C. for 4 h, was tested. After 6 pulses, the average selectivity was 84%, and the yield of isobutylene was 0.67 g/kg catalyst.

EXAMPLE 9

A catalyst was prepared in accordance with the procedure described above using $Sm(NO_3)_3$ as a starting material. In this example, the catalyst, consisting of 10% mol $Cr_2O_3$ supported on $Sm_2(CO_3)_3$, calcined in air at 300° C. for 4 h, was tested. After 6 pulses, the average selectivity was 94%, and the yield of isobutylene was 0.67 g/kg catalyst.

We claim:

1. A catalyst for the oxidative dehydrogenation of hydrocarbons which comprises a chromium oxide support on a lanthanide carbonate, wherein said chromium oxide is chemically bound to the surface of the lanthanide carbonate and is present as a separate crystalline phase.

2. A catalyst according to claim 1, wherein the atomic ratio of chromium to lanthanide is in the range 1:99 to 20:80.

3. A catalyst according to claim 1, wherein said catalyst contains one or more additional components which alter the activity and/or selectivity of said catalyst.

4. A catalyst as claimed in claim 1, wherein the lanthanide is selected from the group consisting of lanthanum, praseodymium and samarium.

5. A catalyst as claimed in claim 1, wherein the lanthanide is lanthanum.

6. A catalyst according to claim 3, wherein said additional components are selected from the group consisting of oxides or carbonates of the metals of groups IA and IIA, the transition metals excluding chromium, lanthanide other than the lanthanide of claim 1, or mixtures thereof.

7. A process for producing a catalyst for the oxidative dehydrogenation of hydrocarbons which comprises the steps of co-precipitating the carbonates of chromium and a lanthanide and heating the co-precipitated carbonates to a temperature sufficient to form and activate a catalyst which comprises chromium oxide supported on a lanthanide carbonate, wherein said chromium oxide is chemically bound to the surface of the lanthanide carbonate and is present as a separate crystalline phase.

8. A process for producing a catalyst for the oxidative dehydrogenation of hydrocarbons which comprises;
a) providing a solution containing ions of chromium and one or more lanthanides;
b) adding a source of carbonate ions to the solution thereby to co-precipitate carbonates of the two metals;
c) separating the co-precipitated carbonates from the solution;
d) washing and drying the co-precipitated carbonates; and
e) heating the co-precipitated carbonates to a temperature sufficient to form and activate a catalyst which comprises chromium oxide supported on a lanthanide carbonate, wherein said chromium oxide is chemically bound to the surface of the lanthanide carbonate and is present as a separate crystalline phase.

9. A process according to claim 8, wherein said co-precipitation of step b) is carried out at a temperature in the range from ambient to 60° C.

10. A process according to claim 8, wherein the activation of the catalyst in step e) is carried out by heating said co-precipitated carbonates in air or an inert atmosphere at a temperature up to 600° C.

11. A process according to claim 10, wherein the the temperature is in the range 200° to 450° C.

12. A process according to claim 7 or claim 8, wherein one or more additional components which alter the activity and/or selectivity of said catalyst are incorporated into the catalyst.

13. A process according to claim 12, wherein the said additional components are incorporated into the catalyst by co-precipitation with said carbonates of chromium and lanthanide.

14. A catalyst according to claim 12, wherein said additional components are selected from the group consisting of oxides or carbonates of the metals of groups IA and IIA, the transition metals excluding chromium, lanthanide other than the lanthanide of claim 1, or mixtures thereof.

15. A process as claimed in claim 8, wherein the concentrations of the chromium and lanthanide ions in the solution of step (a) are such as to provide in the final catalyst product an atomic ratio of chromium to lanthanide in the range 1:99 to 20:80.

16. A process as claimed in claim 7, wherein the lanthanide is selected from the group consisting of lanthanum, praseodymium and samarium.

17. A process as claimed in claim 7, wherein the lanthanide is lanthanum.

* * * * *